United States Patent
Kshirsagar et al.

(10) Patent No.: US 9,145,541 B2
(45) Date of Patent: Sep. 29, 2015

(54) MICROORGANISM CONCENTRATION PROCESS

(75) Inventors: Manjiri T. Kshirsagar, Woodbury, MN (US); Tushar A. Kshirsagar, Woodbury, MN (US); Thomas E. Wood, Stillwater, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 621 days.

(21) Appl. No.: 12/679,063

(22) PCT Filed: Oct. 2, 2008

(86) PCT No.: PCT/US2008/078563
§ 371 (c)(1),
(2), (4) Date: Mar. 19, 2010

(87) PCT Pub. No.: WO2009/046183
PCT Pub. Date: Apr. 9, 2009

(65) Prior Publication Data
US 2010/0248214 A1 Sep. 30, 2010

Related U.S. Application Data

(60) Provisional application No. 60/977,188, filed on Oct. 3, 2007.

(51) Int. Cl.
| | | |
|---|---|---|
| *C12N 1/00* | (2006.01) |
| *C12Q 1/24* | (2006.01) |
| *C12N 11/00* | (2006.01) |
| *C12N 1/02* | (2006.01) |
| *B01J 20/02* | (2006.01) |
| *B01J 20/06* | (2006.01) |
| *B01J 20/28* | (2006.01) |
| *C12N 11/14* | (2006.01) |
| *C12Q 1/04* | (2006.01) |
| *G01N 1/40* | (2006.01) |
| *G01N 33/543* | (2006.01) |

(52) U.S. Cl.
CPC .............. *C12N 1/02* (2013.01); *B01J 20/0229* (2013.01); *B01J 20/06* (2013.01); *B01J 20/2803* (2013.01); *B01J 20/28004* (2013.01); *C12N 11/14* (2013.01); *C12Q 1/04* (2013.01); *C12Q 1/24* (2013.01); *G01N 1/405* (2013.01); *G01N 33/54313* (2013.01)

(58) Field of Classification Search
None
See application file for complete search history.

(56) References Cited

U.S. PATENT DOCUMENTS

| | | | |
|---|---|---|---|
| 3,912,593 A | 10/1975 | Barker et al. | |
| 4,046,712 A | 9/1977 | Cairns et al. | |
| 4,560,660 A | 12/1985 | Geirnaert | |
| 4,618,525 A | 10/1986 | Chamberlain et al. | |
| 4,729,846 A | 3/1988 | Matsui et al. | |
| 5,238,812 A | 8/1993 | Coulter et al. | |
| 5,354,688 A * | 10/1994 | Francis et al. | 435/262 |
| 5,364,766 A | 11/1994 | Mach et al. | |
| 5,462,860 A | 10/1995 | Mach | |
| 5,576,185 A | 11/1996 | Coulter et al. | |
| 5,759,403 A | 6/1998 | Clauss et al. | |
| 6,045,913 A | 4/2000 | Castle | |
| 6,057,488 A | 5/2000 | Koper et al. | |
| 6,150,300 A | 11/2000 | Khare | |
| 6,730,230 B2 | 5/2004 | Cook et al. | |
| 6,764,969 B1 | 7/2004 | Kuhn et al. | |
| 6,861,002 B2 | 3/2005 | Hughes | |
| 7,074,916 B2 | 7/2006 | Bastian et al. | |
| 7,201,841 B2 | 4/2007 | Hughes | |
| 7,422,868 B2 | 9/2008 | Fan et al. | |
| 7,431,904 B2 | 10/2008 | Høj | |
| 2002/0077249 A1 | 6/2002 | Schlegel et al. | |
| 2002/0162798 A1 * | 11/2002 | Johnson et al. | 210/660 |
| 2003/0009014 A1 | 1/2003 | Chiou | |
| 2003/0226443 A1 | 12/2003 | Rajagopalan et al. | |
| 2004/0159605 A1 | 8/2004 | Hughes | |
| 2004/0178142 A1 | 9/2004 | Koslow | |
| 2004/0217061 A1 | 11/2004 | Corzani et al. | |
| 2005/0019755 A1 * | 1/2005 | Marchessault et al. | 435/5 |
| 2005/0020449 A1 | 1/2005 | Blais | |
| 2005/0095189 A1 | 5/2005 | Brey et al. | |
| 2006/0024776 A1 | 2/2006 | McMillian | |

(Continued)

FOREIGN PATENT DOCUMENTS

| | | |
|---|---|---|
| CA | 2056167 | 11/1991 |
| EP | 0093027 | 11/1983 |

(Continued)

OTHER PUBLICATIONS

Ams et al., "Experimental measurements of the adsorption of *Bacillus subtilis* and *Pseudomonas mendocina* onto Fe-oxyhydroxide-coated and uncoated quartz grains" Geomicrobiology Journal, vol. 21, No. 8, pp. 511-519, ISSN: 0149-0451, XP008100501, Dec. 2004.

(Continued)

*Primary Examiner* — Lisa J Hobbs
(74) *Attorney, Agent, or Firm* — Adrian L. Pishko; Stephen L. Crooks

(57) ABSTRACT

A process for capturing or concentrating microorganisms for detection or assay comprises (a) providing a particulate concentration agent that comprises gamma-FeO(OH); (b) providing a fluid sample comprising at least one microorganism strain; and (c) contacting the concentration agent with the sample such that at least a portion of the concentration agent is dispersed in the sample and at least a portion of the at least one microorganism strain is bound to or captured by the concentration agent.

9 Claims, No Drawings

(56) References Cited

U.S. PATENT DOCUMENTS

| | | | |
|---|---|---|---|
| 2006/0144793 | A1 | 7/2006 | Dadachov |
| 2006/0188580 | A1 | 8/2006 | Sacks |
| 2006/0249465 | A1 | 11/2006 | Jin et al. |
| 2006/0292555 | A1 | 12/2006 | Xu et al. |
| 2007/0020649 | A1 | 1/2007 | Tseng et al. |
| 2008/0166792 | A1 | 7/2008 | Attar et al. |
| 2010/0190171 | A1 | 7/2010 | Kshirsagar et al. |
| 2010/0209961 | A1 | 8/2010 | Kshirsagar et al. |
| 2010/0247592 | A1 | 9/2010 | Kshirsagar et al. |
| 2010/0248214 | A1 | 9/2010 | Kshirsagar et al. |

FOREIGN PATENT DOCUMENTS

| | | |
|---|---|---|
| EP | 0391608 | 3/1990 |
| EP | 1524024 | 2/2010 |
| GB | 2228477 | 8/1990 |
| JP | 6-081595 | 10/1994 |
| JP | 2000-014380 | 1/2000 |
| JP | 2001-112497 | 4/2001 |
| JP | 2002-125695 | 5/2002 |
| JP | 2003-210158 | 7/2003 |
| JP | 2005-254123 | 9/2005 |
| WO | WO 02/49684 | 6/2002 |
| WO | WO 03/064330 | 8/2003 |
| WO | WO 2004/068511 | 8/2004 |
| WO | WO 2005/030382 | 4/2005 |
| WO | WO 2006/069712 | 7/2006 |
| WO | WO 2006/072944 | 7/2006 |
| WO | WO 2006/074126 | 7/2006 |
| WO | WO 2006/077020 | 7/2006 |
| WO | WO 2006/090375 | 8/2006 |
| WO | WO 2006/128187 | 11/2006 |
| WO | WO 2008/079800 | 7/2008 |
| WO | WO 2009/026035 | 2/2009 |

OTHER PUBLICATIONS

Berry, E. and Siragusa, G. "Hydroxyapatite Adherence as a Means to Concentrate Bacteria" Applied and Environmental Microbiology, pp. 4069-4074, Oct. 1997.

Brown et al., "Virus Removal by Diatomaceous-Earth Filtration-Part 1", Journal American Water Works Association, Denver, CO, vol. 66, No. 2, pp. 98-102, XP001013356, ISSN: 0003-150X, Jan. 1, 1974.

Chaudhuri et al., "Virus Removal by Diatomaceous Earth Filtration", Journal of Environmental Engineering Division, American Society of Civil Engineers, New York, NY, vol. 100, pp. 937-953, XP001013190, ISSN: 0090-3914, Aug. 1, 1974.

Collins et al., "Development of a rapid detection method for waterborne *Escherichia coli* 0157:H7." XP002510684 Database accession No. PREV200300556872 abstract & Abstracts of the General Meeting of the American Society for Microbiology, vol. 103, 2003, pp. Q-496 URL, 103rd American Society for Microbiology General Meeting; Washington, DC, USA; May 18-22, 2003. ISSN: 1060-2011—Database Biosis [Online], Biosciences Information Service, Philadelphia, PA, US; 2003.

Cullison et al. "Magnetized Carbonyl Iron and Insoluble Zirconium Hydroxide Mixture Facilitates Bacterial Concentration and Separation from Nonfat Dry Milk", Journal of Food Protection, vol. 65, No. 11, pp. 1806-1810, Jun. 2002.

Farrah et al., "Adsorption of Viruses by Diatomaceous Earth Coated with Metallic Oxides and Metallic Peroxides", Wat. Sci. Tec., vol. 24, No. 2, pp. 235-240, 1991.

Farrah et al., "Adsorption of Viruses to Diatomaceous Earth Modified by in situ Precipitation of Metallic Salts", Department of Microbiology and Cell Science, University of Florida, vol. 34, No. 9, pp. 520-521, Jan. 1, 1988.

Farrah et al., "Use of Modified Diatomaceous Earth for Removal and Recovery of Viruses in Water" Applied and Environmental Microbiology, vol. 57, No. 9, pp. 2502-2506, XP001013212 ISSN: 0099-2240, Sep. 1, 1991.

Fass et al., "Silicates: non-specific adsorbents in purification of water from viruses", Pub Med, NCBI, Dev. Biol. Stand; vol. 46, pp. 91-96; 1980.

Fass et al., "Silicates as Nonspecific Adsorbents of Bacteriophage: a Model for Purification of Water from Viruses", Pub Med, NCBI, Appl. Environ. Microbiol., vol. 39 (1), pp. 227-232; Jan. 1980.

Fu et al. "Anatase $TiO_2$ Nanocomposites for Antimicrobial Coatings", J. Phys. Chem. B, vol. 109, pp. 8889-8898 (2005).

Jiang et al., "Adsorption of *Pseudomonoas putida* on Clay Minerals and Iron Oxide" Colloids and Surfaces. B, Biointerfaces, Elsevier, Amsterdam, NL, vol. 54, No. 2, pp. 217-221, XP005858731, ISSN: 0927-7765, Jan. 25, 2007.

Knapp et al., "The Effect of Distribution of Iron-oxyhydroxide Grain Coatings on the Transport of Bacterial Cells in Porous Media", Environmental Geology (Berlin), vol. 33, No. 4, pp. 243-248, XP002510778, ISSN: 0943-0105, Mar. 1998.

Krack et al. "Effect of Growth Phase and Metabolic Activity on the Adhesion of *Escherichia coli* K-12 AB264 to Quartz and Lepidocrocite", Geomicrobiology Journal, vol. 24, No. 3-4, pp. 179-187, XP008100479, ISSN: 0149-0451, 2007.

Lucore et al., "Immobilization with Metal Hydroxides as a Means to Concentrate Food-Borne Bacteria for Detection by Cultural and Molecular Methods", Applied and Environmental Microbiology, vol. 66, No. 5, pp. 1769-1776, May 2000.

Lukasik et al., "Removal of Microorganisms from Water by Columns Containing Sand Coated with Ferric and Aluminum Hydroxides", Wat. Res., vol. 33, No. 3, pp. 769-777, 1999.

Mills et al., "Effect of Solution Ionic Strength and Iron Coatings on Mineral Grains on the Sorption of Bacterial Cells to Quartz Sand", Applied and Environmental Microbiology, vol. 60, No. 9, pp. 3300-3306, XP002510777, ISSN: 0099-2240, 1994.

Rao et al., "Detection of Viruses in Drinking Water by Concentration on Magnetic Iron Oxide", Applied and Environmental Microbiology, vol. 42, No. 3, pp. 421-426, Sep. 1981.

Schindler et al., "Immobilization and Detection of *Listeria monocytogenes*", Applied and Environmental Microbiology, vol. 72, No. 6, pp. 4426-4428, Jun. 2006.

Shah et al., "New Horizons in Purification of Liquids", Soil and Water Pollution Monitoring, Protection and Remediation, 3-23, pp. 369-386, 2006.

Stevens, K. and Jaykus, L-A, "Bacterial Separation and concentration from complex sample matrices: A Review" Critical Reviews in Microbiology, 30 (1), pp. 7-24, 2004.

Takeuchi et al., "High Dispersion Platinum Catalyst by RF Sputtering," Journal of Catalysis, vol. 83, pp. 477-479, 1983.

Taylor et al., "Effect of Food Matrix and Cell Growth on PCR-Based Detection of *Escherichia coli* O157:H7 in Ground Beef", Journal of food Protection, vol. 68, No. 2, pp. 225-232, 2005.

Wegmann et al., "Modification of ceramic microfilters with colloidal zirconia to promote the adsorption of viruses from water", Science Direct, Water Research 42, pp. 1726-1734, 2008.

Bryant, T., "New UD Technology Removes Viruses From Drinking Water", UDaily, Office of Public Relations, University of Delaware, http://udel.edu/PR/UDaily/2007/feb/viruses022607.html, Feb. 26, 2007.

International Search Report, PCT/US2008/078563, International Filing Date Oct. 2, 2008.

Safety data sheet, Iron (III) hydroxide gamma, 17531, Alfa Aesar GmbH & Co. KG, Jan. 22, 2007 pp. 1-3, XP055066640, retrieved from the Internet: hyyp://www.alfa.com/content/msds/English/17531.pdf [retrieved on Jun. 13, 2013].

17531 Iron(III) hydroxide, gamma-phase, p. 1 (of 3), retrieved from the Internet: URL:https://www.alfa.com/en/catalog/17531 [retrieved on Nov. 7, 2014].

CAS: 20344-49—Iron(III) hydroxide, p. 1 (of 3), retrieved from the Internet: URL:https://www.alfa.com/en/cas/20344-49-4 [retrieved on Nov. 7, 2014].

\* cited by examiner

MICROORGANISM CONCENTRATION PROCESS

STATEMENT OF PRIORITY

This application claims the priority of U.S. Provisional Application No. 60/977,188 filed Oct. 3, 2007, the contents of which are hereby incorporated by reference.

FIELD

This invention relates to processes for capturing or concentrating microorganisms such that they remain viable for detection or assay. In other aspects, this invention also relates to diagnostic kits for use in carrying out such concentration processes.

BACKGROUND

Food-borne illnesses and hospital-acquired infections resulting from microorganism contamination are a concern in numerous locations all over the world. Thus, it is often desirable or necessary to assay for the presence of bacteria or other microorganisms in various clinical, food, environmental, or other samples, in order to determine the identity and/or the quantity of the microorganisms present.

Bacterial DNA or bacterial RNA, for example, can be assayed to assess the presence or absence of a particular bacterial species even in the presence of other bacterial species. The ability to detect the presence of a particular bacterium, however, depends, at least in part, on the concentration of the bacterium in the sample being analyzed. Bacterial samples can be plated or cultured to increase the numbers of the bacteria in the sample to ensure an adequate level for detection, but the culturing step often requires substantial time and therefore can significantly delay the assessment results.

Concentration of the bacteria in the sample can shorten the culturing time or even eliminate the need for a culturing step. Thus, methods have been developed to isolate (and thereby concentrate) particular bacterial strains by using antibodies specific to the strain (for example, in the form of antibody-coated magnetic or non-magnetic particles). Such methods, however, have tended to be expensive and still somewhat slower than desired for at least some diagnostic applications.

Concentration methods that are not strain-specific have also been used (for example, to obtain a more general assessment of the microorganisms present in a sample). After concentration of a mixed population of microorganisms, the presence of particular strains can be determined, if desired, by using strain-specific probes.

Non-specific concentration or capture of microorganisms has been achieved through methods based upon carbohydrate and lectin protein interactions. Chitosan-coated supports have been used as non-specific capture devices, and substances (for example, carbohydrates, vitamins, iron-chelating compounds, and siderophores) that serve as nutrients for microorganisms have also been described as being useful as ligands to provide non-specific capture of microorganisms.

Various inorganic materials (for example, hydroxyapatite and metal hydroxides) have been used to non-specifically bind and concentrate bacteria. Physical concentration methods (for example, filtration, chromatography, centrifugation, and gravitational settling) have also been utilized for non-specific capture, with and/or without the use of inorganic binding agents. Such non-specific concentration methods have varied in speed, cost (at least some requiring expensive equipment, materials, and/or trained technicians), sample requirements (for example, sample nature and/or volume limitations), space requirements, ease of use (at least some requiring complicated multi-step processes), suitability for on-site use, and/or effectiveness.

SUMMARY

Thus, we recognize that there is an urgent need for processes for rapidly detecting pathogenic microorganisms. Such processes will preferably be not only rapid but also low in cost, simple (involving no complex equipment or procedures), and/or effective under a variety of conditions (for example, with varying types of sample matrices, varying bacterial loads, and varying sample volumes).

Briefly, in one aspect, this invention provides a process for non-specifically concentrating the strains of microorganisms (for example, strains of bacteria, fungi, yeasts, protozoans, viruses (including both non-enveloped and enveloped viruses), and bacterial endospores) present in a sample, such that the microorganisms remain viable for the purpose of detection or assay of one or more of the strains. The process comprises (a) providing a particulate concentration agent that comprises gamma-FeO(OH) (also known as lepidocrocite); (b) providing a fluid sample comprising at least one microorganism strain; and (c) contacting (preferably, by mixing) the concentration agent with the sample such that at least a portion of the concentration agent is dispersed in the sample and at least a portion of the at least one microorganism strain is bound to or captured by the concentration agent. Preferably, the process further comprises detecting the presence of the at least one bound microorganism strain (for example, by culture-based, microscopy/imaging, genetic, bioluminescence-based, or immunologic detection methods) and/or segregating (preferably, by gravitational settling) the resulting microorganism-bound concentration agent. The process can optionally further comprise separating the resulting segregated concentration agent from the sample.

The process of the invention does not target a specific microorganism strain. Rather, it has been discovered that certain relatively inexpensive, inorganic materials can be surprisingly effective in capturing a variety of microorganisms. Such materials can be used to concentrate the microorganism strains present in a sample (for example, a food sample) in a non-strain-specific manner, so that one or more of the microorganism strains (preferably, one or more strains of bacteria) can be more easily and rapidly assayed.

The process of the invention is relatively simple and low in cost (requiring no complex equipment or expensive strain-specific materials) and can be relatively fast (preferred embodiments capturing at least about 70 percent (more preferably, at least about 80 percent; most preferably, at least about 90 percent) of the microorganisms present in a sample in less than about 30 minutes, relative to a corresponding control sample without concentration agent). In addition, the process can be effective with a variety of microorganisms (including pathogens such as both gram positive and gram negative bacteria) and with a variety of samples (different sample matrices and, unlike at least some prior art methods, even samples having low microorganism content and/or large volumes). Thus, at least some embodiments of the process of the invention can meet the above-cited urgent need for low-cost, simple processes for rapidly detecting pathogenic microorganisms under a variety of conditions.

In another aspect, the invention also provides a diagnostic kit for use in carrying out the process of the invention, the kit comprising (a) a particulate concentration agent that comprises gamma-FeO(OH); (b) a testing container (preferably, a sterile testing container); and (c) instructions for using the concentration agent in carrying out the process of the invention. Preferably, the diagnostic kit further comprises one or more components selected from microorganism culture media, lysis reagents, buffers, and genetic and bioluminescence detection assay components.

In yet another aspect, the invention provides a process comprising (a) providing a particulate concentration agent that comprises at least one iron oxide or iron oxyhydroxide that comprises microparticle agglomerates comprising acicular crystallites that are less than 1 micrometer in largest dimension; (b) providing a fluid sample comprising at least one microorganism strain; and (c) contacting (preferably, by mixing) the concentration agent with the sample such that at least a portion of the concentration agent is dispersed in the sample and at least a portion of the at least one microorganism strain is bound to or captured by the concentration agent.

In still another aspect, the invention also provides a kit comprising (a) a particulate concentration agent that comprises at least one iron oxide or iron oxyhydroxide that comprises microparticle agglomerates comprising acicular crystallites that are less than 1 micrometer in largest dimension; (b) a testing container; and (c) instructions for using the concentration agent in carrying out the process of claim 1.

DETAILED DESCRIPTION

Definitions

As used in this patent application:

"sample" means a substance or material that is collected (for example, to be analyzed); "sample matrix" means the components of a sample other than microorganisms; "detection" means the identification of at least a component of a microorganism, which thereby determines that the microorganism is present;

"genetic detection" means the identification of a component of genetic material such as DNA or RNA that is derived from a target microorganism;

"immunologic detection" means the identification of an antigenic material such as a protein or a proteoglycan that is derived from a target microorganism; "microorganism" means any cell having genetic material suitable for analysis or detection (including, for example, bacteria, yeasts, viruses, and bacterial endospores);

"microorganism strain" means a particular type of microorganism that is distinguishable through a detection method (for example, microorganisms of different genera, of different species within a genera, or of different isolates within a species); and "target microorganism" means any microorganism that is desired to be detected.

Concentration Agent

Concentration agents suitable for use in carrying out the process of the invention include those particulate concentration agents that comprise gamma-FeO(OH) (also known as lepidocrocite). Such concentration agents have been found to be surprisingly more effective than other iron-containing concentration agents in capturing gram-negative bacteria, which are the microorganisms of greatest concern in regard to food- and water-borne illnesses and human bacterial infections. The concentration agents can further include (in addition to gamma-FeO(OH)) other components (for example, boehmite ($\alpha$-AlO(OH)), clays, iron oxides, and silicon oxides), but, preferably, such other components do not significantly interfere with the intimate contact of the sample and the concentration agent when carrying out the process of the invention. Thus, the concentration agents preferably consist essentially of gamma-FeO(OH).

Concentration or capture using such concentration agents is generally not specific to any particular strain, species, or type of microorganism and therefore provides for the concentration of a general population of microorganisms in a sample. Specific strains of microorganisms can then be detected from among the captured microorganism population using any known detection method with strain-specific probes. Thus, the concentration agents can be used for the detection of microbial contaminants or pathogens (particularly food-borne pathogens such as bacteria) in clinical, food, environmental, or other samples.

Gamma-FeO(OH) is known and can be chemically synthesized by known methods (for example, by oxidation of ferrous hydroxide at neutral or slightly acidic pHs, as described for purposes of magnetic tape production in U.S. Pat. No. 4,729,846 (Matsui et al.), the description of which is incorporated herein by reference). Gamma-FeO(OH) is also commercially available (for example, from Alfa Aesar, A Johnson Matthey Company, Ward Hill, Mass., and from Sigma-Aldrich Corporation, St. Louis, Mo.).

In carrying out the process of the invention, the concentration agents are used in particulate form, more preferably comprising microparticles (preferably, microparticles having particle sizes (largest dimension) in the range of about 3 micrometers (more preferably, about 5 micrometer; most preferably, about 10 micrometers) to about 100 micrometers (more preferably, about 80 micrometers; even more preferably, about 50 micrometers; most preferably, about 35 micrometers; where any lower limit can be paired with any upper limit of the range). Preferably, the particles are agglomerates of smaller particles. The particles preferably comprise crystallites that are less than about 1 micrometer in size (preferably, less than about 0.5 micrometer in size). The crystallites can be present as acicular crystallites, as raft-like structures comprising acicular crystallites, or as combinations of the acicular crystallites and raft-like structures. The concentration agents preferably have a surface area as measured by the BET (Brunauer-Emmett-Teller) method (calculation of the surface area of solids by physical adsorption of nitrogen gas molecules) that is greater than about 25 square meters per gram ($m^2/g$), more preferably greater than about 50 $m^2/g$. and most preferably greater than about 75 $m^2/g$.

The preferred agglomerated form of the particles can provide the adsorptive capabilities of fine particle systems without the handling and other hazards often associated with fine particles. In addition, such agglomerate particles can settle readily in fluid and thus can provide rapid separation of microorganisms from a fluid phase (as well as allowing low back pressure if used in filtration applications).

Such an agglomerate structure can be induced in iron-bearing oxide or oxy-hydroxide particles by several methods that involve preparing small component crystallites. In general, fine iron oxy-hydroxide of both the goethite and the lepidocrocite forms can be generated by an aerial oxidation of ferrous hydroxide or ferrous carbonate. Lepidocrocite is the more preferred form and can be generated by an aerial oxidation of ferrous hydroxide or carbonate while maintaining lower pHs (for example, from about pH 3 to about pH 5). Higher pH values can lead to the goethite form. The resulting small crystallites can spontaneously agglomerate to the desired agglomerated form if the agitation rate during the oxidation is low (for example, magnetic stirring). If small crystallites remain that are not in the agglomerated form after the synthesis, the particle dispersion can be spray dried to form agglomerates that after drying (for example, at about 90 to 150° C.) can remain in the agglomerated form.

Sample

The process of the invention can be applied to a variety of different types of samples, including, but not limited to, medical, environmental, food, feed, clinical, and laboratory samples, and combinations thereof. Medical or veterinary samples can include, for example, cells, tissues, or fluids from a biological source (for example, a human or an animal) that are to be assayed for clinical diagnosis. Environmental samples can be, for example, from a medical or veterinary facility, an industrial facility, soil, a water source, a food preparation area (food contact and non-contact areas), a laboratory, or an area that has been potentially subjected to bioterrorism. Food processing, handling, and preparation area samples are preferred, as these are often of particular concern in regard to food supply contamination by bacterial pathogens.

The sample is used in the process of the invention in the form of a fluid (for example, a liquid, a gas, or a dispersion or suspension of solid or liquid in liquid or gas). Samples obtained in the form of a liquid or in the form of a dispersion or suspension of solid in liquid, for example, can be used directly, or can be concentrated (for example, by centrifugation) or diluted (for example, by the addition of a buffer (pH-controlled) solution). Samples in the form of a solid or a semi-solid can be extracted by a method such as, for example, washing or rinsing with, or suspending or dispersing in, a fluid medium (for example, a buffer solution), so as to form a fluid sample for use in the process. Samples can be taken from surfaces (for example, by swabbing and/or rinsing).

Examples of samples that can be used (either directly or after treatment to provide a fluid sample) in carrying out the process of the invention include foods (for example, fresh produce or ready-to-eat lunch or "deli" meats), beverages (for example, juices or carbonated beverages), potable water, and biological fluids (for example, whole blood or a component thereof such as plasma, a platelet-enriched blood fraction, a platelet concentrate, or packed red blood cells; cell preparations (for example, dispersed tissue, bone marrow aspirates, or vertebral body bone marrow); cell suspensions; urine, saliva, and other body fluids; bone marrow; lung fluid; cerebral fluid; wound exudate; wound biopsy samples; ocular fluid; spinal fluid; and the like), as well as lysed preparations, such as cell lysates, which can be formed using known procedures such as the use of lysing buffers, and the like. Preferred samples include foods, beverages, potable water, biological fluids, and combinations thereof (with foods, beverages, potable water, and combinations thereof being more preferred).

Sample volume can vary, depending upon the particular application. For example, when the process of the invention is used for a diagnostic or research application, the volume of the sample can typically be in the microliter range (for example, 10 μL or greater). When the process is used for a food pathogen testing assay or for potable water safety testing, the volume of the sample can typically be in the milliliter to liter range (for example, 100 milliliters to 3 liters). In an industrial application, such as bioprocessing or pharmaceutical formulation, the volume can be tens of thousands of liters.

The process of the invention can isolate microorganisms from a sample in a concentrated state and can also allow the isolation of microorganisms from sample matrix components that can inhibit detection procedures that are to be used. In all of these cases, the process of the invention can be used in addition to, or in replacement of, other methods of microorganism concentration. Thus, optionally, cultures can be grown from samples either before or after carrying out the process of the invention, if additional concentration is desired.

Contacting

The process of the invention can be carried out by any of various known or hereafter developed methods of providing contact between two materials so as to form a dispersion. For example, the particulate concentration agent can be added to the sample, or the sample can be added to the particulate concentration agent. A spatula or dipstick or other article bearing particulate concentration agent can be immersed in a sample solution, a sample solution can be poured onto a film bearing particulate concentration agent, or a sample solution can be poured into a tube or well containing particulate concentration agent, or the like. In all cases, at least a portion of the particulate concentration agent becomes dispersed in the sample.

Preferably, however, the particulate concentration agent and the sample are combined (using any order of addition) in any of a variety of containers (optionally but preferably, a capped, closed, or sealed container; more preferably, a capped test tube, bottle, or jar). Suitable containers for use in carrying out the process of the invention will be determined by the particular sample and can vary widely in size and nature. For example, the container can be small, such as a 10 microliter container (for example, a test tube) or larger, such as a 100 milliliter to 3 liter container (for example, an Erlenmeyer flask or a polypropylene large-mouth bottle). The container, the concentration agent, and any other apparatus or additives that contact the sample directly can be sterilized (for example, by controlled heat, ethylene oxide gas, hydrogen peroxide, or radiation) prior to use, in order to reduce or prevent any contamination of the sample that might cause detection errors. The amount of concentration agent that is sufficient to capture or concentrate the microorganisms of a particular sample for successful detection will vary (depending upon, for example, the nature and form of the concentration agent and sample volume) and can be readily determined by one skilled in the art. For example, 10 milligrams of concentration agent per milliliter of sample can be useful for some applications.

If desired, contacting can be effected by passing particulate concentration agent at least once through a sample (for example, by relying upon gravitational settling over a period of, for example, about 10 minutes). Contact can be enhanced by mixing (for example, by stirring, shaking, or use of a rocking platform) such that the particles of concentration agent repeatedly pass or settle through a substantial portion of the sample. For small volumes on the order of microliters (typically less than 0.5 milliliter), mixing can be rapid such as by vortexing or "nutation," for example as described in U.S. Pat. No. 5,238,812 (Coulter et al.), the description of which is incorporated herein by reference. For larger volumes on the order of greater than or equal to 0.5 milliliters (typically 0.5 milliliter to 3 liters), mixing can be achieved by gently tumbling the particulate concentration agent and the sample in an "end over end" fashion, for example as described in U.S. Pat. No. 5,576,185 (Coulter et al.), the description of which is incorporated herein by reference. Such tumbling can be accomplished, for example, by means of a device configured to hold a test tube or other type of reaction vessel and to slowly rotate the test tube or vessel in an "end over end" manner. Contacting can be carried out for a desired period (for example, for sample volumes of about 100 milliliters or less, up to about 60 minutes of contacting can be useful;

preferably, about 15 seconds to about 10 minutes or longer; more preferably, about 15 seconds to about 5 minutes).

Thus, in carrying out the process of the invention, mixing (for example, agitation, rocking, or stirring) and/or incubation (for example, at ambient temperature) are optional but preferred, in order to increase microorganism contact with the concentration agent. A preferred contacting method includes both mixing (for example, for about 15 seconds to about 5 minutes) and incubating (for example, for about 3 minutes to about 30 minutes) a microorganism-containing fluid sample with particulate concentration agent. If desired, one or more additives (for example, lysis reagents, bioluminescence assay reagents, nucleic acid capture reagents (for example, magnetic beads), microbial growth media, buffers (for example, to disperse or extract a solid sample), microbial staining reagents, washing buffers (for example, to wash away unbound material), elution agents (for example, serum albumin), surfactants (for example, Triton™ X-100 nonionic surfactant available from Union Carbide Chemicals and Plastics, Houston, Tex.), mechanical abrasion/elution agents (for example, glass beads), and the like) can be included in the combination of concentration agent and sample.

Segregation and/or Separation

Optionally but preferably, the process of the invention further comprises segregation of the resulting microorganism-bound concentration agent. Such segregation preferably can be achieved by relying, at least in part, upon gravitational settling (gravity sedimentation; for example, over a time period of about 5 minutes to about 30 minutes). In some cases, however, it can be desirable to accelerate segregation (for example, by centrifugation or filtration) or to use combinations of any of the segregation methods.

The process of the invention can optionally further comprise separating the resulting microorganism-bound concentration agent and the sample. This can involve removal or separation of the supernatant that results upon segregation. Separation of the supernatant can be carried out by numerous methods that are well-known in the art (for example, by decanting or siphoning, so as to leave the microorganism-bound concentration agent at the bottom of the container or vessel utilized in carrying out the process).

The process of the invention can be carried out manually (for example, in a batch-wise manner) or can be automated (for example, to enable continuous or semi-continuous processing).

Detection

A variety of microorganisms can be concentrated and, optionally but preferably, detected by using the process of the invention, including, for example, bacteria, fungi, yeasts, protozoans, viruses (including both non-enveloped and enveloped viruses), bacterial endospores (for example, *Bacillus* (including *Bacillus anthracis, Bacillus cereus*, and *Bacillus subtilis*) and *Clostridium* (including *Clostridium botulinum, Clostridium difficile*, and *Clostridium perfringens*)), and the like, and combinations thereof (preferably, bacteria, yeasts, fungi, viruses, bacterial endospores, and combinations thereof; more preferably, bacteria, yeasts, viruses, bacterial endospores, and combinations thereof; even more preferably, bacteria, viruses, bacterial endospores, and combinations thereof; yet more preferably, gram-negative bacteria, gram-positive bacteria, non-enveloped viruses (for example, norovirus, poliovirus, hepatitis A virus, rhinovirus, and combinations thereof), bacterial endospores, and combinations thereof; most preferably, gram-negative bacteria and combinations thereof). The process has utility in the detection of pathogens, which can be important for food safety or for medical, environmental, or anti-terrorism reasons. The process can be particularly useful in the detection of pathogenic bacteria (for example, both gram negative and gram positive bacteria), as well as various yeasts, molds, and mycoplasmas (and combinations of any of these).

Genera of target microorganisms to be detected include, but are not limited to, *Listeria, Escherichia, Salmonella, Campylobacter, Clostridium, Helicobacter, Mycobacterium, Staphylococcus, Shigella, Enterococcus, Bacillus, Neisseria, Shigella, Streptococcus, Vibrio, Yersinia, Bordetella, Borrelia, Pseudomonas, Saccharomyces, Candida*, and the like, and combinations thereof. Samples can contain a plurality of microorganism strains, and any one strain can be detected independently of any other strain. Specific microorganism strains that can be targets for detection include *Escherichia coli, Yersinia enterocolitica, Yersinia pseudotuberculosis, Vibrio cholerae, Vibrio parahaemolyticus, Vibrio vulnificus, Listeria monocytogenes, Staphylococcus aureus, Salmonella enterica, Saccharomyces cerevisiae, Candida albicans, Staphylococcal enterotoxin* ssp, *Bacillus cereus, Bacillus anthracis, Bacillus atrophaeus, Bacillus subtilis, Clostridium perfringens, Clostridium botulinum, Clostridium difficile, Enterobacter sakazakii, Pseudomonas aeruginosa*, and the like, and combinations thereof (preferably, *Staphylococcus aureus, Salmonella enterica, Candida albicans, Bacillus atrophaeus, Bacillus subtilis, Escherichia coli*, human-infecting non-enveloped enteric viruses for which *Escherichia coli* bacteriophage is a surrogate, and combinations thereof).

Microorganisms that have been captured or bound (for example, by adsorption) by the concentration agent can be detected by essentially any desired method that is currently known or hereafter developed. Such methods include, for example, culture-based methods (which can be preferred when time permits), microscopy (for example, using a transmitted light microscope or an epifluorescence microscope, which can be used for visualizing microorganisms tagged with fluorescent dyes) and other imaging methods, immunological detection methods, and genetic detection methods. The detection process following microorganism capture optionally can include washing to remove sample matrix components.

Immunological detection is detection of an antigenic material derived from a target organism, which is commonly a biological molecule (for example, a protein or proteoglycan) acting as a marker on the surface of bacteria or viral particles. Detection of the antigenic material typically can be by an antibody, a polypeptide selected from a process such as phage display, or an aptamer from a screening process.

Immunological detection methods are well-known and include, for example, immunoprecipitation and enzyme-linked immunosorbent assay (ELISA). Antibody binding can be detected in a variety of ways (for example, by labeling either a primary or a secondary antibody with a fluorescent dye, with a quantum dot, or with an enzyme that can produce chemiluminescence or a colored substrate, and using either a plate reader or a lateral flow device).

Detection can also be carried out by genetic assay (for example, by nucleic acid hybridization or primer directed amplification), which is often a preferred method. The captured or bound microorganisms can be lysed to render their genetic material available for assay. Lysis methods are well-known and include, for example, treatments such as sonication, osmotic shock, high temperature treatment (for example, from about 50° C. to about 100° C.), and incubation with an enzyme such as lysozyme, glucolase, zymolose, lyticase, proteinase K, proteinase E, and viral enolysins.

Many commonly-used genetic detection assays detect the nucleic acids of a specific microorganism, including the DNA and/or RNA. The stringency of conditions used in a genetic detection method correlates with the level of variation in nucleic acid sequence that is detected. Highly stringent conditions of salt concentration and temperature can limit the detection to the exact nucleic acid sequence of the target. Thus microorganism strains with small variations in a target nucleic acid sequence can be distinguished using a highly stringent genetic assay. Genetic detection can be based on nucleic acid hybridization where a single-stranded nucleic acid probe is hybridized to the denatured nucleic acids of the microorganism such that a double-stranded nucleic acid is produced, including the probe strand. One skilled in the art will be familiar with probe labels, such as radioactive, fluorescent, and chemiluminescent labels, for detecting the hybrid following gel electrophoresis, capillary electrophoresis, or other separation method.

Particularly useful genetic detection methods are based on primer directed nucleic acid amplification. Primer directed nucleic acid amplification methods include, for example, thermal cycling methods (for example, polymerase chain reaction (PCR), reverse transcriptase polymerase chain reaction (RT-PCR), and ligase chain reaction (LCR)), as well as isothermal methods and strand displacement amplification (SDA) (and combinations thereof; preferably, PCR or RT-PCR). Methods for detection of the amplified product are not limited and include, for example, gel electrophoresis separation and ethidium bromide staining, as well as detection of an incorporated fluorescent label or radio label in the product. Methods that do not require a separation step prior to detection of the amplified product can also be used (for example, real-time PCR or homogeneous detection).

Bioluminescence detection methods are well-known and include, for example, adenosine triphosphate (ATP) detection methods including those described in U.S. Pat. No. 7,422,868 (Fan et al.), the descriptions of which are incorporated herein by reference.

Since the process of the invention is non-strain specific, it provides a general capture system that allows for multiple microorganism strains to be targeted for assay in the same sample. For example, in assaying for contamination of food samples, it can be desired to test for *Listeria monocytogenes*, *Escherichia coli*, and *Salmonella* all in the same sample. A single capture step can then be followed by, for example, PCR or RT-PCR assays using specific primers to amplify different nucleic acid sequences from each of these microorganism strains. Thus, the need for separate sample handling and preparation procedures for each strain can be avoided.

Diagnostic Kit

A diagnostic kit for use in carrying out the process of the invention comprises (a) an above-described concentration agent; (b) a testing container (preferably, a sterile testing container); and (c) instructions for using the concentration agent in carrying out the process of the invention. Preferably, the diagnostic kit further comprises one or more components selected from microorganism culture or growth media, lysis reagents, buffers, bioluminescence detection assay components (for example, luminometer, lysis reagents, luciferase enzyme, enzyme substrate, reaction buffers, and the like), genetic detection assay components, and combinations thereof. A preferred lysis reagent is a lytic enzyme supplied in a buffer, and preferred genetic detection assay components include one or more primers specific for a target microorganism.

For example, a preferred embodiment of the diagnostic kit of the invention contains a particulate concentration agent (for example, in a sterile disposable container such as a glass or polypropylene vial), in combination with instructions for using said agent in carrying out the process of the invention (for example, by mixing the concentration agent with a fluid sample to be analyzed, allowing the concentration agent to settle by gravity, removing the resulting supernatant, and detecting the presence of at least one concentration agent-bound target microorganism strain). The concentration agent optionally can be hydrated in a small volume of buffer with preservative to improve stability during storage and transportation and/or can be contained/aliquoted in a tear-open, sealed pouch to prevent contamination. The concentration agent can be in the form of a dispersion or suspension in a liquid or can be in powder form. Preferably, the diagnostic kit comprises pre-measured aliquots (for example, based upon sample volume) of particulate concentration agent (more preferably, contained in one or more tear-open, sealed pouches).

EXAMPLES

Objects and advantages of this invention are further illustrated by the following examples, but the particular materials and amounts thereof recited in these examples, as well as other conditions and details, should not be construed to unduly limit this invention.

Materials

Gamma-FeO(OH) (60 mesh powder, less than 250 microns in diameter; catalog number 17531), $Fe_2O_3$ (powder; catalog number 10716), and $Fe_3O_4$ (powder) were purchased from Alfa Aesar (A Johnson Matthey Company, Ward Hill, Mass.). FeO (10 mesh powder, less than 2 mm in diameter) was purchased from Sigma-Aldrich Corporation (catalog number 40,086-6, St. Louis, Mo.). All microorganism stock cultures were purchased from The American Type Culture Collection (ATCC, Manassas, Va.).

Samples of each of the iron-containing powders were examined using scanning electron microscopy (SEM). The $Fe_3O_4$ sample was found to comprise predominantly blocky, acicular, vermicular crystals, with the smallest crystals being below about 5 micrometers in size and the largest being about 44-45 micrometers in primary dimension. The vermicular crystals comprised smaller crystals joined at low angle grain boundaries and laced with uniform, sub-micrometer pores.

The $Fe_2O_3$ particles were very similar in size and shape to the $Fe_3O_4$ particles, with the exception that the $Fe_2O_3$ particle sample contained a larger percentage of large (about 50-70 micrometer) agglomerates of blocky, vermicular crystals.

The gamma-FeO(OH) sample comprised agglomerates of smaller particles, and the agglomerates ranged in size from slightly less than about 10 micrometers to about 60 micrometers. The smaller particles in the agglomerates generally comprised clusters of even smaller particles that were acicular and about 0.25-0.75 micron in length with the other two dimensions being about 0.05 micrometer to about 0.25 micrometer in size. In some cases the acicular crystals were agglomerated into larger, about 0.5 micrometer to about 1 micrometer raft-like structures. These raft-like structures were similarly agglomerated into larger clusters.

The FeO sample comprised large particles (for example, greater than about 150 micrometers in size), as well as smaller particles (for example, less than about 10 micrometers in size). The majority of the sample was present as about 30 to 70 micrometer particles. The particles did not appear to be polycrystalline.

BET (Brunauer-Emmett-Teller) Surface Area Measurements

Approximately 0.1-1.0 g of concentration agent was transferred to a 1.3 centimeter (0.5 inch) diameter sample tube available from Micromeritics, Inc. of Norcross, Ga. and degassed using a system commercially available from Micromeritics under the trade designation VACPREP 061 at least overnight at 110° C. under vacuum (below 10 mTorr or 0.015 mbar). After degassing, the concentration agent was allowed to cool for 10 minutes under vacuum at ambient temperature (that is, 20° C. to 25° C.) and then loaded onto a surface area and porosity analyzer commercially available from Micromeritics under the trade designation TRISTAR 3000.

An 8-point adsorption isotherm was set up with relative pressures ($P/P_o$) starting at about 0 up to about 0.3 (see table below for target pressures and points). No first "pressure fixed dose" or maximum volume increment was set. The "absolute pressure tolerance" was set at 5 mm Hg, and the "relative pressure tolerance" was set at 5.0 percent. The "fast evacuation" option was not used, and a 120 second leak test was performed. With the analyzer's dewar of liquid nitrogen lowered (that is, the concentration agent was not in the liquid nitrogen), an evacuation time of 0.1 hour was implemented before a free space measurement. After the free space measurement, an outgassing test was performed for 180 seconds. The dewar was raised for analysis (that is, the tube containing the concentration agent was placed in liquid nitrogen). At 77.350 K (the temperature of liquid nitrogen), $P_o$ was measured initially and at 120 minute intervals (if needed) during the analysis. The gas adsorptive properties using a standard Pstat versus temperature table for nitrogen gas were set at the following values: non-ideality factor, 0.0000620; density conversion factor, 0.0015468; molecular cross-sectional area, 0.162 $nm^2$. BET adsorption surface areas were calculated based on the quantity of $N_2$ adsorbed at each relative pressure during the 8-point adsorption isotherm.

The following table shows the pressures and points used for the analysis.

Target Pressures and Points

| Point | Relative Pressure P/Po |
|---|---|
| 1 | 0.025 |
| 2 | 0.03 |
| 3 | 0.05 |
| 4 | 0.1 |
| 5 | 0.15 |
| 6 | 0.2 |
| 7 | 0.25 |
| 8 | 0.3 |

The resulting BET surface areas were 81.43 $m^2/g$ for gamma-FeO(OH), 1.64 $m^2/g$ for $Fe_2O_3$, and 1.74 $m^2/g$ for $Fe_3O_4$.

Microorganism Concentration Test Method

An isolated microorganism colony was inoculated into 5 mL BBL™ Trypticase™ Soy Broth (Becton Dickinson, Sparks, Md.) and incubated at 37° C. for 18-20 hours. This overnight culture at ~$10^9$ colony forming units per mL was diluted in adsorption buffer (containing 5 mM KCl, 1 mM $CaCl_2$, 0.1 mM $MgCl_2$, and 1 mM $K_2HPO_4$) at pH 7.2 to obtain $10^3$ microorganisms per mL dilution. A 1.1 mL volume of the microorganism dilution was added to separate, labeled sterile 5 mL polypropylene tubes (BD Falcon™, Becton Dickinson, Franklin Lakes, N.J.) containing 10 mg of concentration agent, each of which was capped and mixed on a Thermolyne Maximix Plus™ vortex mixer (Barnstead International, Iowa). Each capped tube was incubated at room temperature (25° C.) for 15 minutes on a Thermolyne Vari Mix™ shaker platform (Barnstead International, Iowa). After the incubation, each tube was allowed to stand on the lab bench for 10 minutes to settle the concentration agent. Control sample tubes containing 1.1 mL of the microorganism dilution without concentration agent were treated in the same manner. The resulting settled concentration agent and/or supernatant (and the control samples) were then used for analysis.

The settled concentration agent was re-suspended in 1 mL sterile Butterfield's Buffer solution (pH 7.2±0.2; monobasic potassium phosphate buffer solution; VWR Catalog Number 83008-093, VWR, West Chester, Pa.) and plated on 3M™ Petrifilm™ Aerobic Count Plates culture medium (dry, rehydratable; 3M Company, St. Paul., Minn.) according to the manufacturer's instructions. Aerobic count was quantified using a 3M™ Petrifilm™ Plate Reader (3M Company, St. Paul., Minn.). Results were calculated using the following formula:

Percent CFU/mL in Re-suspended Concentration Agent=(number of colonies from plated re-suspended concentration agent)/(number of colonies from plated untreated control sample)×100

(where CFU=Colony Forming Unit, which is a unit of live or viable microorganisms). Results were then reported in terms of percent capture of microorganisms by the concentration agent using the formula below:

Capture Efficiency or Percent Capture=Percent CFU/mL in Re-suspended Concentration Agent For comparison purposes, in at least some cases 1 mL of the supernatant was removed and plated undiluted or diluted 1:10 in Butterfield's Buffer solution and plated onto 3M™ Petrifilm™ Aerobic Count Plates culture medium. Aerobic count was quantified using a 3M™ Petrifilm™ Plate Reader (3M Company, St. Paul., Minn.). Results were calculated using the following formula:

Percent CFU/mL in Supernatant=(number of colonies from plated supernatant)/(number of colonies from plated untreated control sample)×100

(where CFU=Colony Forming Unit, which is a unit of live or viable microorganisms). When the microorganism colonies and the concentration agent were similar in color (providing little contrast for the plate reader), results were based upon the supernatant and were then reported in terms of percent capture of microorganisms by the concentration agent using the formula below:

Capture Efficiency or Percent Capture=100−Percent CFU/mL in Supernatant

Example 1 and Comparative Examples 1-3

Using the above-described microorganism concentration test method, 10 mg of various iron-containing concentration agents were tested separately for bacterial concentration against a target microorganism, the gram-negative bacterium *Salmonella enterica* subsp. *enterica* serovar *Typhimurium* (ATCC 35987). The results are shown in Table 1 below.

TABLE 1

| Example No. | Microorganism | Concentration Agent | Percent Capture | Standard Deviation |
|---|---|---|---|---|
| C-1 | *Salmonella* | FeO | 17.0 | 2.1 |
| C-2 | *Salmonella* | $Fe_2O_3$ | 65.0 | 4.1 |
| C-3 | *Salmonella* | $Fe_3O_4$ | 65.0 | 4.1 |
| 1 | *Salmonella* | Gamma-FeO(OH) | 93.7 | 1.4 |

Examples 2-4

Using the above-described microorganism concentration test method, different weights per unit volume of gamma-FeO(OH) were tested separately for bacterial concentration of the target microorganism, *Salmonella enterica* subsp. *enterica serovar Typhimurium* (ATCC 35987). The results are shown in Table 2 below (standard deviation for all samples less than 10 percent).

TABLE 2

| Example No. | Microorganism | Concentration Agent | Amount of Concentration Agent (mg/mL) | Percent Capture |
|---|---|---|---|---|
| 2 | *Salmonella* | Gamma-FeO(OH) | 1 | 73 |
| 3 | *Salmonella* | Gamma-FeO(OH) | 5 | 91 |
| 4 | *Salmonella* | Gamma-FeO(OH) | 10 | 96 |

Example 5

Using the above-described microorganism concentration test method, 10 mg of gamma-FeO(OH) was tested for bacterial concentration of the target microorganism, *Staphylococcus aureus* (ATCC 6538), a gram-positive bacterium. The results are shown in Table 3 below (standard deviation less than 10 percent).

TABLE 3

| Example No. | Microorganism | Concentration Agent | Percent Capture |
|---|---|---|---|
| 5 | *Staphylococcus* | Gamma-FeO(OH) | 96 |

Examples 6-8

Using the above-described microorganism concentration test method, 10 mg of gamma-FeO(OH) was tested for bacterial concentration of the target microorganism, *Salmonella enterica* subsp. *enterica serovar Typhimurium* (ATCC 35987) for 5, 10, and 15 minutes of incubation. The results are shown in Table 4 below (standard deviation for all samples less than 10 percent).

TABLE 4

| Example No. | Microorganism | Concentration Agent | Incubation Time (minutes) | Percent Capture |
|---|---|---|---|---|
| 6 | *Salmonella* | Gamma-FeO(OH) | 5 | 85 |
| 7 | *Salmonella* | Gamma-FeO(OH) | 10 | 95 |
| 8 | *Salmonella* | Gamma-FeO(OH) | 15 | 97 |

Example 9

Using the above-described microorganism concentration test method, 10 mg of gamma-FeO(OH) was tested for yeast concentration of the target microorganism, *Candida albicans* ($10^2$ CFU/mL; ATCC MYA-2876). The resulting materials were plated on 3M™ Petrifilm™ Yeast and Mold Count Plate culture medium (dry, rehydratable; 3M Company, St. Paul, Minn.) and incubated for 5 days according to the manufacturer's instructions. Isolated yeast colonies were counted manually, and percent capture was calculated as described above. The results are shown in Table 5 below (standard deviation less than 10 percent).

TABLE 5

| Example No. | Microorganism | Concentration Agent | Percent Capture |
|---|---|---|---|
| 9 | *Candida* | Gamma-FeO(OH) | 100 |

Examples 10 and 11

10 mg samples of gamma-FeO(OH) concentration agent were tested for concentration of the target bacterial endospores *Bacillus atrophaeus* (ATCC 9372) and *Bacillus subtilis* (ATCC 19659). The above-described microorganism concentration test method was utilized with the following modifications: the overnight cultures had $0.9 \times 10^2$ CFU/mL *Bacillus atrophaeus* and $4.5 \times 10^2$ CFU/mL *Bacillus subtilis*, respectively; the resulting supernatants were plated undiluted; the settled concentration agent with bound *Bacillus atrophaeus* was resuspended in 2 mL sterile Butterfield's Buffer solution and plated in duplicate (1 mL each); the settled concentration agent with bound *Bacillus subtilis* was resuspended in 5 mL sterile Butterfield's Buffer solution and plated in duplicate (1 mL each). Capture efficiencies were calculated based on counts from the plated supernatants and determined to be 99 percent for *Bacillus atrophaeus* and 96 percent for *Bacillus subtilis* (standard deviation for all samples less than 10 percent).

Example 12

10 mg of gamma-FeO(OH) concentration agent was tested for concentration of the target non-enveloped, bacteria-infecting virus, *Escherichia coli* bacteriophage MS2 (ATCC 15597-B1; which is often used as a surrogate for various human-infecting, non-enveloped enteric viruses). A double layer agar method (described below) was used to assay for capture of the *Escherichia coli* bacteriophage MS2 (ATCC 15597-B1) using *Escherichia coli* bacteria (ATCC 15597) as host.

*Escherichia coli* bacteriophage MS2 stock was diluted tenfold serially in sterile 1× adsorption buffer (containing 5 mM KCl, 1 mM $CaCl_2$, 0.1 mM $MgCl_2$, and 1 mM $K_2HPO_4$) at pH 7.2 to obtain $10^3$ plaque forming units per milliliter (PFUs/mL). A 1.0 mL volume of the resulting bacteriophage dilution was added to a labeled sterile 5 mL polypropylene tube (BD Falcon™, Becton Dickinson, Franklin Lakes, N.J.) containing 10 mg of concentration agent and mixed on a Thermolyne Maximix Plus™ vortex mixer (Barnstead International, Iowa). The capped tube was incubated at room temperature (25° C.) for 15 minutes on a Thermolyne Vari Mix™ shaker platform (Barnstead International, Iowa). After the incubation, the tube was allowed to stand on the lab bench for 10 minutes to settle the concentration agent. A control sample tube containing 1.0 mL of the bacteriophage dilution without concentration agent was treated in the same manner. The resulting settled concentration agent and supernatant (and the control sample) were then used for analysis.

100 microliters of the supernatant was removed and assayed for bacteriophage using the double layer agar method described below. An additional 800 microliters of supernatant was removed and discarded. One hundred microliters of the settled concentration agent was also assayed for bacteriophage.

Double Layer Agar Method:

A single colony of *Escherichia coli* bacteria (ATCC 15597) was inoculated into 25 mL sterile 3 weight percent tryptic soy broth (Bacto™ Tryptic Soy Broth, Becton Dickinson and Company, Sparks, Md.; prepared according to manufacturer's instructions) and incubated at 37° C. in a shaker incubator (Innova™ 44, New Brunswick Scientific Co., Inc., Edison, N.J.) set at 250 revolutions per minute (rpm) overnight. 750 microliters of this overnight culture was used to inoculate 75 mL sterile 3 weight percent tryptic soy broth. The resulting culture was incubated at 37° C. in the shaker incubator set at 250 rpm to obtain *Escherichia coli* cells in the exponential phase as measured by absorbance at 550 nm (absorbance values 0.3-0.6) using a SpectraMax M5 spectrophotometer (Molecular Devices, Sunnyvale, Calif.). The cells were incubated on ice until used for assay.

One hundred microliters of the above-described bacteriophage test samples were mixed with 75 microliters of the ice-incubated *Escherichia coli* (host bacteria) cells and incubated at room temperature (25° C.) for 5 minutes. The resulting samples were mixed with 5 mL sterile molten top agar (3 weight percent tryptic soy broth, 1.5 weight percent NaCl, 0.6 weight percent agar; prepared that day and maintained in a 48° C. waterbath). The mixture was then poured on top of bottom agar (3 weight percent tryptic soy broth, 1.5 weight percent NaCl, 1.2 weight percent agar) in petridishes. The molten agar component of the mixture was allowed to solidify for 5 minutes, and the petridishes or plates were inverted and incubated at 37° C. The plates were visually inspected after overnight incubation, and, in three independent experiments, those plates containing settled concentration agent (as well as the control plate) showed the presence of bacteriophage plaques. Capture efficiencies were calculated based on counts from the plated supernatants and determined to be 93 percent (standard deviation less than 10 percent).

Example 13

Apple juice was purchased from a local grocery store (Cub Foods, St. Paul). Apple juice (11 g) was weighed in a sterile glass dish and added to 99 mL sterile Butterfield's Buffer. The resulting combination was mixed by swirling for 1 minute and was spiked with two bacterial cultures, each at a 1 CFU/mL concentration, using 18-20 hour overnight cultures (bacterial stocks) of *Salmonella enterica* subsp. *enterica serovar Typhimurium* (ATCC 35987) and *Escherichia coli* (ATCC 51813). Serial dilutions of the bacterial stocks had been made in 1× adsorption buffer as described above.

Using the above-described microorganism concentration test method, a 10 mL volume of the spiked apple juice sample was added to a sterile 50 mL conical polypropylene centrifuge tube (BD Falcon™, Becton Dickinson, Franklin Lakes, N.J.) containing 100 mg of gamma-FeO(OH) concentration agent and tested for bacterial capture/concentration of the target microorganism, *Salmonella* (in the presence of the *Escherichia coli*, a competitor microorganism). The resulting supernatant was removed, and the settled concentration agent was transferred to another sterile 50 mL tube containing 2 mL sterile 3 weight percent tryptic soy broth (Bacto™ Tryptic Soy Broth, Becton Dickinson and Company, Sparks, Md.; prepared according to manufacturer's instructions). The tube was loosely capped, and its contents were mixed and incubated at 37° C. After overnight incubation, the resulting broth mixture was tested for the presence of *Salmonella* using a RapidChek™ *Salmonella* lateral flow immunoassay test strip from SDI (Strategic Diagnostics, Inc., Newark, Del.). Visual inspection of the test strip showed it to be positive for *Salmonella*.

Nucleic acid detection by polymerase chain reaction (PCR) was also carried out for the microorganism-containing broth mixture. 1 mL of the above-described overnight-incubated, concentration agent-containing broth was assayed as a test sample for the presence of *Salmonella* by using a TaqMan™ ABI *Salmonella enterica* Detection Kit from Applied Biosystems (Foster City, Calif.). As a control sample, 1 mL of the 18-20 hour overnight culture (stock) of *Salmonella enterica* subsp. *enterica serovar Typhimurium* (ATCC 35987) was also assayed. PCR testing was conducted in a Stratagene Mx3005P™ QPCR (quantitative PCR) System (Stratagene Corporation, La Jolla, Calif.) by using the following cycle conditions per cycle for 45 cycles: 25° C. for 30 seconds, 95° C. for 10 minutes, 95° C. for 15 seconds, and 60° C. for 1 minute. An average (n=2) cycle threshold value (CT value) of 17.71 was obtained for the control sample. An average (n=2) CT value of 18.04 was obtained for the test sample, indicating a positive PCR reaction and confirming the presence of *Salmonella*.

The referenced descriptions contained in the patents, patent documents, and publications cited herein are incorporated by reference in their entirety as if each were individually incorporated. Various unforeseeable modifications and alterations to this invention will become apparent to those skilled in the art without departing from the scope and spirit of this invention. It should be understood that this invention is not intended to be unduly limited by the illustrative embodiments and examples set forth herein and that such examples and embodiments are presented by way of example only, with the scope of the invention intended to be limited only by the claims set forth herein as follows:

We claim:

1. A process comprising:
   (a) providing a particulate concentration agent that consists essentially of gamma-FeO(OH) that comprises microparticle agglomerates comprising acicular crystallites that are less than 1 micrometer in largest dimension, wherein the microparticle agglomerates have particle sizes in the range of 3 micrometers to 100 micrometers in largest dimension;
   (b) providing a fluid sample comprising at least one microorganism strain selected from strains of bacteria, yeasts, bacterial endospores, bacteriophages, and combinations thereof;
   (c) contacting said concentration agent with said sample such that at least a portion of said concentration agent is dispersed in said sample and at least a portion of said at least one microorganism strain is bound to or captured by said concentration agent to provide a microorganism-bound concentration agent;
   (d) segregating the resulting microorganism-bound concentration agent, wherein said segregating is effected by gravitational settling of the microorganism-bound concentration agent, wherein the gravitational settling is achieved over a time period of about 5 minutes to about 30 minutes; and
   (e) detecting the presence of at least one viable bound microorganism.

2. The process of claim 1, wherein said microorganism strain is selected from strains of bacteria, yeasts, and combinations thereof.

3. The process of claim 2, wherein said microorganism strain is selected from strains of bacteria and combinations thereof.

4. The process of claim 1, wherein said microorganism strain is selected from strains of gram-negative bacteria and combinations thereof.

5. The process of claim 1, wherein said contacting is carried out by mixing said concentration agent and said sample.

6. The process of claim 1, wherein said detecting is carried out by a method selected from culture-based methods, microscopy and other imaging methods, genetic detection methods, immunologic detection methods, bioluminescence-based detection methods, and combinations thereof.

7. The process of claim 1, wherein said process further comprises separating the resulting segregated concentration agent from said sample.

8. A kit comprising (a) a particulate concentration agent that consists essentially of gamma-FeO(OH) that comprises microparticle agglomerates comprising acicular crystallites that are less than 1 micrometer in largest dimension, wherein the microparticle agglomerates have particle sizes in the range of 3 to 100 micrometers in largest dimension, and wherein the microparticle agglomerates have particles sizes in a range from 3 micrometers to 100 micrometers in largest dimension; (b) a testing container; (c) instructions for using said concentration agent in carrying out the process of claim 1; and (d) at least one of a genetic detection assay component, a bioluminescence detection assay component, a microorganism count plate, an antibody, a polypeptide, an aptamer, a fluorescent dye, or an enzyme.

9. The method of claim 1, wherein the contacting is carried out for a period of about 15 seconds to about 5 minutes.

* * * * *

UNITED STATES PATENT AND TRADEMARK OFFICE
CERTIFICATE OF CORRECTION

PATENT NO. : 9,145,541 B2  
APPLICATION NO. : 12/679063  
DATED : September 29, 2015  
INVENTOR(S) : Manjiri Kshirsagar It is certified that error appears in the above-identified patent and that said Letters Patent is hereby corrected as shown below:

Title Page

Page 2, Column 2,
Under "Other Publications", delete "Pseudomonoas" and insert -- Pseudomonas --, therefor.

Specification

Column 8,
Line 65, delete "enolysins." and insert -- endolysins. --, therefor.

Claims

Column 17,
Lines 13-15, in Claim 6, delete "microscopy and other imaging methods, genetic detection methods, immunologic detection methods, bioluminescence-based detection methods," and insert -- immunologic detection methods, --, therefor.

Signed and Sealed this  
Fifth Day of April, 2016

Michelle K. Lee  
*Director of the United States Patent and Trademark Office*